United States Patent [19]

Bridges et al.

[11] Patent Number: 5,387,757
[45] Date of Patent: Feb. 7, 1995

[54] TOMATOES WITH REDUCED EXPRESSION OF POLYGALACTURONASE

[75] Inventors: Ian G. Bridges, Slater, Iowa; Wolfgang W. Schuch, Crowthorne; Donald Grierson, Shepshed, both of England

[73] Assignee: Zeneca Limited, London, England

[21] Appl. No.: 41,337

[22] Filed: Apr. 1, 1993

Related U.S. Application Data

[63] Continuation of Ser. No. 577,049, Sep. 4, 1990, abandoned, which is a continuation of Ser. No. 350,362, May 11, 1989, abandoned, which is a continuation-in-part of Ser. No. 119,614, Nov. 12, 1987.

[30] Foreign Application Priority Data

May 11, 1989 [GB] United Kingdom ............... 8811115

[51] Int. Cl.⁶ ..................... A01H 5/08; A01H 5/10
[52] U.S. Cl. ......................... 800/205; 800/255; 800/DIG. 44,DIG. 64; 435/320.1; 536/23.6
[58] Field of Search ............... 800/205, 250, DIG. 64, 800/255, DIG. 44; 935/64, 67; 435/172.3, 320.1, 240.4; 536/23.6

[56] References Cited

U.S. PATENT DOCUMENTS

4,801,540  1/1989  Hiatt et al. .................. 435/172.3

OTHER PUBLICATIONS

Slater, et al (1985) Plant Molecular Biology 5:137–147.
Ecker et al (1986) Proc. Natl. Acad. Sci., USA 83:5372–5376.
Giovannoni et al (1989) The Plant Cell 1:53–63.
Simmonds *Principles of Crop Improvement* Longman Group Limited, New York, 1979, pp. 124–125.
Horsch et al (1985) Science 227:1229–1231.
Della Penna, et al (1986) Proc. Natl. Acad. Sci., USA 83:6420–6424.

*Primary Examiner*—Che S. Chereskin
*Attorney, Agent, or Firm*—Cushman Darby & Cushman

[57] ABSTRACT

Fruit, especially tomatoes, having lowered expression of fruit-softening enzymes caused by antisense gene expression, and seeds therefrom.

4 Claims, 7 Drawing Sheets

FIG. IA1

```
                                                              M  V  I  Q  R  N  S
AATCTTTTTCAATAGACAAGTTTAAAAACCATACCATATAACAATATATCATGGTTATCCAAAGGAATAG
         10        20        30        40        50        60        70

I  L  L  I  I  F  A  S  S  I  S  T  C  R  S
TATTCTCCTTCTCATTATTTTTGCTTCATCAATTTCAACTTGTAGAA
         80        90       100       110       120

N  V  I  D  D  N  L  F  K  Q  V  Y  D  N  I  L  E  Q  E  F  A  H  D
GCAATGTTATTGATGACAATCTATTCAAACAAGTTTATGATAATATTCTTGAACAAGAATTTGCTCATGA
        130       140       150       160       170       180       190

F  Q  A  Y  L  S  Y  L  S  K  N  I  E  S  N  N  N
TTTTCAAGCTTATCTTTCTTATTTGAGCAAAAATATTGAAAGCAACAATA
        200       210       220       230       240

I  D  K  V  D  K  N  G  I  K  V  I  N  V  L  S  F  G  A  K  G  D  G
ATATTGACAAGGTTGATAAAAATGGGATTAAAGTGATTAATGTACTTAGCTTTGGAGCTAAGGGTGATGG
        250       260       270       280       290       300       310

K  T  Y  D  N  I  A  F  E  Q  A  W  N  E  A  C  S
AAAAACATATGATAATATTGCATTTGAGCAAGCATGGAATGAAGCATGTT
        320       330       340       350       360
```

FIG. IA2

```
          S   R   T   P   V   Q   F   V   V   P   K   N   K   N   Y   L   L   K   Q   I   T   F   S
CATCTAGAACACCTGTTCAATTTGTGGTTCCTAAAAACAAGAATTATCTTCTCAAGCAAATCACCTTTCA
                    370                 380                 390                 400                 410                 420                 430
  G   P   C   R   S   S   I   S   V   K   I   F   G   S   L   E   A
GGTCCATGCAGATCTTCTATTTCAGTAAAGATTTTTGGATCCTTAGAAG
            440                 450                 460                 470                 480
    S   S   K   I   S   D   Y   K   D   R   R   L   W   I   A   F   D   S   V   Q   N   L   V
CATCTAGTAAAATTTCAGACTACAAAGATAGAAGGCTTTGGATTGCTTTTGATAGTGTTCAAAATTAGTT
                    490                 500                 510                 520                 530                 540                 550
  V   G   G   G   T   I   N   G   N   G   Q   V   W   W   P   S
GTTGGAGGAGGAACTATCAATGGCAATGGACAAGTATGGTGGCCAA
            560                 570                 580                 590                 600
    S   C   K   I   N   K   S   L   P   C   R   D   A   P   T   A   L   T   F   W   N   C   K
GTTCTTGCAAAATAAATAAATCACTGCCATGCAGGATGCACCAACGGCCCTTAACCTTCTGGAATTGCAAA
                    610                 620                 630                 640                 650                 660                 670
  N   L   K   V   N   N   L   K   S   K   N   A   Q   Q   I   H   I
AATTTGAAAGTGAATAATCTAAAGAGTAAAAATGCACAACAAATTCATA
            680                 690                 700                 710                 720
    K   F   F   S   C   T   N   V   V   A   S   N   L   M   I   N   A   S   A   K   S   P   N
TCAAATTTGAGTCATGCACTAATGTTGTAGCTTCAAATTTGATGATCAATGCTTCAGCAAAGAGCCCAAAT
                    730                 740                 750                 760                 770                 780                 790
  T   D   G   V   H   V   S   N   T   Q   Y   I   Q   I   S   D   T
ACTGATGGAGTCCATGTATCAAATACTCAATATTCAAATATCTGATA
            800                 810                 820                 830                 840
```

FIG. 1B1

```
 I   I   G   T   G   D   D   C   I   S   I   V   S   G   S   Q   N   V   Q   A   T   N   I
CTATTATTGGAACAGGTGATGATTGTATTTCAATTGTTTCTGGATCTCAAAATGTGCAGGCCACAAATATT
    850             860             870             880             890             900             910

T   C   G   P   G   H   G   I   S   I   G   S   L   G   S   G   N
ACTTGTGGTCCAGGTCATGGTATAAGTATTGGAAGCTTAGGATCTGGAA
    920             930             940             950             960

S   E   A   Y   V   S   N   V   T   V   N   E   A   K   I   I   G   A   E   N   G   V   R
ATTCAGAAGCTTATGTGTCTAATGTTACTGTTAATGAAGCCAAAATTATCGGTGCCGAAAATGGAGTTAGG
    970             980             990            1000            1010            1020            1030

I   K   T   W   Q   G   G   S   G   Q   A   S   N   I   K   F   L
ATCAAGACTTGGCAGGGAGGATCTGGACAAGCTAGCAACATCAAATTTC
   1040            1050            1060            1070            1080

N   V   E   M   Q   D   V   K   Y   P   I   I   I   D   Q   N   Y   C   D   R   V   E   P
TGAATGTGGAAATGCAAGACGTTAAGTATCCCATAATTATAGACCAAAACTATTGTGATCGAGTTGAACCA
   1090            1100            1110            1120            1130            1140            1150

C   I   Q   Q   F   S   A   V   Q   V   K   N   V   V   Y   E   N
TGTATACAACAGTTTTCAGCAGTTCAAGTGAAAAAATGTGGTGTATGAGA
   1160            1170            1180            1190            1200
```

FIG. IB2

```
  I   K   G   T   S   A   T   K   V   A   I   K   F   D   C   S   T   N   F   P   C   E   G
ATATCAAGGGCACAAGTGCAACAAGGTGGCCATAAAAATTTGATTGCAGCACAAACTTTCCATGTGAAGGA
         1210        1220        1230        1240        1250        1260        1270

I   I   M   E   N   I   N   L   V   G   E   S   G   K   P   S   E
ATTATAATGGAGAATATAAATTTAGTAGGGGAAAGTGGAAAACCATCAG
         1280        1290        1300        1310        1320

A   T   C   K   N   V   H   F   N   N   A   E   H   V   T   P   H   C   T   S   L   E   I
AGGCTACGTGCAAAAAATGTCCATTTTAACAATGCTGAACATGTTACACCACACTGCACTTCACTAGAAATT
         1330        1340        1350        1360        1370        1380        1390

S   E   D   E   A   L   L   Y   N   Y   *
TCAGAGGATGAAGCTCTTTTGTATAATTTATACTATAGATCT
         1400        1410        1420        1430        1440

TCAATATATAGCAGATATGATATATCACAATAAACAAATCTATATCTATGTATTGAATAATTATTATTAAT
         1450        1460        1470        1480        1490        1500        1510

ATGTACGGATTGAAGTTTAATAAGACTACTATGTATTTCTATTTTCTA
         1520        1530        1540        1550        1560

GTCAAAAAGTTTGACGATTGTACTTTTTAATGTACAAAAATAAAATGGTTATTTTATATGAAAAAAAAA
         1570        1580        1590        1600        1610        1620        1630
AAAAAA
```

FIG. 2A

```
CTTTAACTGATTGTCTTGAGCTTCTTGATCTGTCAGTTGATTTAGTATGTGATTCAATTGCAGCAATTGAT
         10        20        30        40        50        60        70

AAGAGAAGTCGTTCGGAGCATGCCAAAGTTGGCTAAGTGGTG
         80        90       100       110       120
                                                       M   I   N   G   T   N
TGCTTACTAACCACGTTACGTGCTTGATGAGCTTGATTCCTTTACTAAAGCTATGATAAATGGAACGAAT
        130       140       150       160       170       180       190
 L   D   E   L   I   S   R   A   K   V   A   L   A   M   L   A   S
CTTGATGAGTTGATCTCCGAGAGCTAAGGTAGCATTGGCGATGCTTGCGT
        200       210       220       230       240
 V   T   T   P   N   D   E   V   L   R   P   G   L   G   K   M   P   S   W   V   S   S   R
CTGGTGACAACTCCAAATGATGAAGTTTTGAGGCCGGGTTTAGGAAAAATGCCATCTTGGGTGAGTTCGAG
        250       260       270       280       290       300       310
 D   R   K   L   M   E   S   S   G   K   D   I   G   A   N   A   V
GATAGGAAGCTGATGGAGAGTTCGGGTAAGGACATTGGAGCGAATGCAG
        320       330       340       350       360
 V   A   K   D   G   T   G   K   Y   R   T   L   A   E   A   V   A   A   A   P   D   K   S
TGGTGGCAAAAGATGGAACAGGGAAATATCGAACACTTGCTGAAGCTGTTGCTGCAGCACCAGATAAGAGT
        370       380       390       400       410       420       430
 K   T   R   Y   V   I   Y   V   K   R   G   T   Y   K   E   N   V
AAGACGCGTTATGTAATTTATGTAAAGAGGGGAACTTATAAAGAGAATG
        440       450       460       470       480
```

FIG. 2BI

```
  Q   L   V   A   R   K   P   G   K   Y   Q   Q   N   M   V   I   A   Q   G   R   T   D   P
GCCAGCTCGTAGCTAGAAAAACCGGGTAAATACCAGCAAAACATGGTGATCGCACAAGGCAGGACGGACCCA
            850             860             870             880             890             900             910

N   Q   A   T   G   T   S   I   Q   F   C   D   I   I   A   S   P
AATCAGGCCACGGGGACATCAATTCAGTTTTGTGATATAATAGCAAGTC
            920             930             940             950             960

D   L   K   P   V   V   K   E   F   P   T   Y   L   G   R   P   W   K   K   Y   S   R   T
CTGACCTAAAACCAGTCGTGAAAGAATTCCCAACATATCTTGGTAGGCCATGGAAAAATATTCAAGAACT
            970             980             990            1000            1010            1020            1030

V   V   M   E   S   S   L   G   G   L   I   D   P   S   G   W   A
GTAGTGATGGAATCATCATTGGGGTTGGTCTCATTGATCCATCGGGTTGGG
           1040            1050            1060            1070            1080

E   W   H   G   D   F   A   L   K   T   L   Y   Y   G   E   F   M   N   N   G   P   G   A
CTGAGTGGCACGGAGATTTGCGTTAAAGACATTGTATTATGGTGAATTTATGAATAATGGACCTGGTGCT
           1090            1100            1110            1120            1130            1140            1150

G   T   S   K   R   V   K   W   P   G   Y   H   V   I   T   D   P
GGTACTAGTAAGCGTGTCAAGTGGCCCTGCTATCATGTCATTACTGACC
           1160            1170            1180            1190            1200

A   E   A   M   S   F   T   V   A   K   L   I   Q   G   G   S   W   L   R   S   T   D   V
CCGCTGAAGCTATGTCATTCACTGTGGCTAAGCTGATTCAGGGCGGATCATGGTTGAGGTCTACTGACGTG
           1210            1220            1230            1240            1250            1260            1270

A   Y   V   D   G   L   Y   D   Y   S   D   I   K   L   L   F   V
GCGTATGTGGATGGATTATATGATTATAGTGATATAAAATTACTCTTTG
           1280            1290            1300            1310            1320
```

FIG. 2B2

```
 Y   V   T   R   H   L   *
TTTATGTAACAAGACATCTTTAAAAAGTTCAAAGTAAGTAGTAGTAATATATCCATATGAAGTGCCACATG
       1330         1340         1350         1360         1370         1380         1390

AGCAGGGCAGAGCGGATTAAGTGTCTAAAGCATAACACACAACTCTAGT
       1400         1410         1420         1430         1440

GTGACAAGCATTTACATGGCTCATTCCCTTACTACTAAGTCGTCAATAAGTTCAGTTAAGGGGTTCATAAGT
       1450         1460         1470         1480         1490         1500         1510

TAATATACGTATATATATTTATGTTGGCGATAAAGCTGAACTGATGATG
       1520         1530         1540         1550         1560

CTTTAATGTAATTATAGTTTTTCTGAAAAAGGATATGTGTAATATATTAGGTTTTTCCCTGATGTTTATGGTTGT
       1570         1580         1590         1600         1610         1620         1630

GGGTGGTGGTTATGATAAAAATATGCAAGATGAAAAAAAAAAAAAA
       1640         1650         1660         1670         1680
```

TOMATOES WITH REDUCED EXPRESSION OF POLYGALACTURONASE

This application is a continuation of Ser. No. 07/577,049, filed Sept. 4, 1990, now abandoned, which in turn is a continuation of Ser. No. 07/350,362, filed May 11, 1989, now abandoned, which in turn is a continuation-in-part of application Ser. No. 07/119,614, filed Nov. 12, 1987.

This invention relates to novel fruit and seeds, and more specifically but not exclusively to novel tomato fruit and seeds produced by genetic modification of the natural tomato plant.

In our co-pending European patent specification No 87309853.7 (now published as 271988) we disclose plants, in particular tomato plants, that have been genetically modified by inclusion of DNA constructs capable of expressing RNA complementary to RNA encoding fruit-softening enzymes. We have now shown that such tomato plants are able to produce fruit and fertile seed. Furthermore fruit of the selfed progeny of such plants show surprising properties, which may include an unexpectedly high level of inhibition of such fruit-softening enzymes.

According to the present invention we provide fruit, especially tomato fruit, having a reduced level of expression of one or more fruit-ripening enzymes, resulting from the presence in the plant genome of DNA capable of generating antisense RNA complementary to the RNA that generates such fruit-ripening enzymes. Preferably such enzymes are fruit-softening enzymes, eg cell wall softening enzymes. We further provide fertile seed, derived from such fruit, which may be cultured to produce similar fruit.

Fruit according to our invention may be obtained by growing and cropping, using conventional methods, the tomato plants described in our European Patent Application No 87309853.7.

Methods for making such plants, by genetic manipulation of known tomato plants, are fully described in the aforesaid European Patent Application No 271988 and in U.S. application Ser. 119614, the complete disclosures of which applications are incorporated herein by reference.

BRIEF DESCRIPTION OF THE DRAWINGS

FIGS. 1 and 2 correspond to FIGS. 1 and 3 from application No. 07/119,614. FIG. 1 shows the base sequence for polygalacturonase CONA pTOM6. FIG. 2 shows the base sequence for pectin methylesterase cDNA clone pPE1.

A convenient method of obtaining such plants is to grow the seeds from tomato fruit according to the invention. we have deposited samples of such seeds with the National Collections of Industrial and Marine Bacteria (hereinafter NCIMB), Torry Research Station, PO Box 31, 135 Abbey Road, Aberdeen AB9 8DG, Scotland, under the reference numbers 40015 and 40134.

Fruit ripening is a complex physiological and biochemical process. It requires the activation of specific genes which are required to give fruit the desirable characteristics important for human consumption, and for industrial processing for consumption. In tomatoes, the end product of the mature fruit is characterised by good, intense and even colour production, specific flavour components and texture suitable for the intended end use (consumption fresh or industrial processing). In biochemical terms these attributes are brought about through the action of enzymes that are responsible for the breakdown of chlorophyll and the synthesis of lycopene $\beta$-carotene for colour production, the synthesis of flavour components through lypoxygenase, the synthesis of enzymes involved in the maintenance of water and mineral balance, enzymes controlling vitamin production, and most importantly for the purposes of the present invention, the production of cell wall degrading enzymes leading to fruit softening.

Preferred fruit according to our invention show reduced levels of expression of the polygalacturonase or the pectin methylesterase gene, or both. This may result from the presence in the genome of one, or several, antisense constructs to either or both genes.

Both pectinesterase and polygalacturonase are involved in the biochemical conversion of pectic cell wall substances during fruit ripening. Pectins demethylated by pectinesterase are believed to be the substrate for polygalacturonase. According to one hypothesis, polygalacturonase solubilises pectic fragments during early ripening stages, and reduces the molecular weight of pectic fragments during later stages of ripening. In fruit according to the invention, the reduction in molecular weight of solubilised pectin is inhibited.

Other enzymes that may be involved in cell wall metabolism, especially cell wall breakdown in ripening fruit, include the following:

xylanases; $\alpha$-galactosidase; $\beta$-galactosidase; cellulase ($\beta$-1,4-glucanase); peroxidase; hemicellulase; isoperoxidase; glucosidases; mannosidases; arabinosidases; $\beta$-fructofuranosidases; trehalase; $\beta$-xylosidase; acid phosphatase; rhaminase; $\beta$-1,3-glucanase; enzymes of calcium metabolism; arabinofuranosidase.

As well as tomatoes, these enzymes, or some of them, may be active in fruit ripening of other fruit besides tomatoes, for example strawberries, melons, cantaloups, peppers and avocados. Accordingly, our invention includes such fruit having a reduced level of expression of any of the aforesaid enzymes.

Preliminary results indicate that tomatoes of the invention having a reduced level of expression of polygalacturonase retain their firmness for a longer period after harvesting than similar tomatoes having normal levels of expression of fruit softening enzymes. They are consequently expected to soften more slowly on the plant, be harder at the time of harvesting and have a longer shelf life, with potentially increased resistance to infection. It is useful to be able to harvest fruit later when flavour, aroma and colour may have developed more fully. Fruit according to our invention may also show increased solids content and altered pectin and cell wall components, with consequent processing advantages. These advantages include energy savings during tomato puree production, increased insoluble solids, and improved gelling qualities and colour of puree.

Seeds according to our invention may be obtained from fruit according to our invention by conventional methods. For example, tomato seeds are separated from the pulp of the ripe fruit and dried, following which they may be stored for one or more seasons. The fruit of our invention may be sold for immediate consumption, raw or cooked, or processed by canning or conversion to soup, sauce or paste. Equally, they may be used to provide seeds according to the invention.

The tomato plants described in European Patent Application No 87309853.7 are heterozygous for the antisense constructs. The seeds obtained from self fertilisation of such plants are a population in which the antisense constructs behave like single Mendelian genes and are distributed according to Mendelian principles: eg, where such a plant contains only one copy of the construct, 25% of the seeds contain two copies of the construct, 50% contain one copy and 25% contain no copy at all. Thus not all the offspring of selfed tomato plants according to European Patent Application No 87309853.7 produce fruit and seeds according to the present invention, and those which do may themselves be either heterozygous or homozygous for the defining trait. Some homozygous fruit according to the invention (eg those obtained from NCIB 40134) are found to show extremely low levels of expression of the fruit-ripening enzyme, eg 5% or less as compared with similar known fruit.

It is convenient to maintain a stock of seed which is homozygous for the antisense construct. All crosses of such seed stock will contain at least one copy of the construct, and self-fertilized progeny will contain two copies, i.e. be homozygous in respect of the character. Such homozygous seed stock may be conventionally used as one parent in F1 crosses to produce heterozygous seed for marketing. Such seed, and fruit derived from it, form further aspects of our invention. It is possible according to our invention to transform two or more plants with different antisense constructs and to cross the progeny of the resulting lines, so as to obtain seed of plants which contain two or more antisense constructs leading to reduced expression of two or more fruit-ripening enzymes.

The following examples illustrate our invention.

EXAMPLE 1

Example 40 of our European Patent Application No 87309853.7 describes the preparation of a tomato plant containing the PG antisense vector pJR16A incorporated in its genome. This plant (referenced as GR16, and derived from *Lycopersicon esculentum* Mill cv Ailsa Craig) was grown in a growth room under standard conditions suitable for growing tomatoes. The flowers were self-fertilised, and 15 resulting fruit collected. Analysis of these by the method of G A Tucker, N G Robertson, D Grierson, (European Journal of Biochemistry, 112 p 119–124, 1980) indicated a low level of expression of the polygalacturonase enzyme, approximately 10% of that in corresponding conventional tomato fruit at similar stage of development. Fruit were also tested for firmness, and showed increased firmness. throughout ripening. Seeds from the fruit were separated from the pulp, allowed to dry in air at room temperature (about 20° C.) and stored dry in brown paper envelopes at room temperature. About 400 of the resulting seeds were deposited with the NCIMB under reference 40015.

EXAMPLE 2

Twelve seeds produced as in Example 1 were taken, grown to maturity and self-fertilized. Plant tissue from each of the 12 resulting seedlings was tested by Southern blot analysis as described in experiment 40 of European Patent Application No 87309853.7. Homozygotic and heterozygotic plants were identified. Seed from homozygous plants was collected, appropriately labelled and stored for future use. Seeds of one such plant, coded GR 105, was deposited with the NCIMB under reference 40134. Analysis of fruit of the plant GR 105 by the method of G A Tucker, N G Robertson, D Grierson, (European Journal of Biochemistry, 112 p 119–124, 1980) indicated an exceptionally low level of expression of the polygalacturonase enzyme, less than 1% of that in corresponding conventional tomato fruit at a similar stage of development.

Another way of obtaining homozygous seed would be to backcross GR16, or a similar transformant, or offspring thereof, to the untransformed Ailsa Craig variety. Standard genetic analysis then permits identification of parent seed homozygous for the antisense construct.

We claim:

1. A tomato fruit having a reduced level of expression of polygalacturonase, resulting from the presence in the plant genome of DNA capable of generating antisense RNA complementary to polygalacturonase mRNA, where the reduced level of expression of polygalacturonase is less than 1% of that of similar unmodified tomatoes at a corresponding development stage.

2. A fruit as claimed in claim 1 which is homozygous for polygalacturonase antisense construct.

3. A seed of a fruit as claimed in claim 1 or 2.

4. A seed as claimed in claim 3 which was deposited with NCIMB under the accession number 40134.

* * * * *